US007011411B2

United States Patent
Shibutani et al.

(10) Patent No.: US 7,011,411 B2
(45) **Date of Patent: *Mar. 14, 2006**

(54) EYE'S OPTICAL CHARACTERISTIC MEASURING SYSTEM

(75) Inventors: Masahiro Shibutani, Tokyo-to (JP); Katsuhiko Kobayashi, Tokyo-to (JP); Gaku Takeuchi, Tokyo-to (JP); Yumi Kubotera, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 236 days.

This patent is subject to a terminal disclaimer.

(21) Appl. No.: 10/364,820

(22) Filed: Feb. 11, 2003

(65) Prior Publication Data

US 2003/0156259 A1 Aug. 21, 2003

(30) Foreign Application Priority Data

Feb. 15, 2002 (JP) ............................ 2002-039155

(51) Int. Cl.
*A61B 3/10* (2006.01)

(52) U.S. Cl. ........................ 351/211; 351/205; 351/215

(58) Field of Classification Search ................ 351/200, 351/205, 206, 210, 211, 213, 214, 215, 221, 351/246, 237, 239
See application file for complete search history.

(56) References Cited

U.S. PATENT DOCUMENTS 4,740,071 A * 4/1988 Kobayashi .................. 351/206
5,546,142 A * 8/1996 Kobayashi .................. 351/237
5,677,750 A * 10/1997 Qi ............................. 351/205
6,273,566 B1 8/2001 Kobayashi et al. ......... 351/221
6,565,210 B1 * 5/2003 Kobayashi et al. ......... 351/214
6,623,117 B1 * 9/2003 Shibutani et al. ........... 351/211

* cited by examiner

*Primary Examiner*—Eric F. Winakur
*Assistant Examiner*—John R. Sanders
(74) *Attorney, Agent, or Firm*—Nields & Lemack

(57) ABSTRACT

An eye's optical characteristic measuring system, comprising a target projecting system for projecting a target image to an ocular fundus of an eye under test, a photodetection optical system for guiding the target image to a photoelectric detector, a simulation image calculating unit for calculating images of the target image to be formed when a plurality of target images of different sizes are independently projected to the fundus of the eye under test based on light amount intensity distribution of the target image detected at the photoelectric detector, and a visual acuity calculating unit having a predetermined threshold value and used for detecting light amount distribution characteristics from each of the light amount intensity distribution in a predetermined longitudinal direction of a plurality of target images calculated at the simulation image calculating unit and for calculating a visual acuity value of a person under test from an intersection of the light amount distribution characteristics and the threshold value.

4 Claims, 5 Drawing Sheets

CONTRAST DISTRIBUTION
S-MT30(u)
S-MT20(u)
S-MT10(u)
(%)
100
90
80
70
60
50
40
30
20
10
0
log(D.V.A.)
-1 -0.8 -0.6 -0.4 -0.2 0 u10 0.4 0.6 0.8 1

EYE'S OPTICAL CHARACTERISTIC MEASURING SYSTEM

BACKGROUND OF THE INVENTION

The present invention relates to an eye's optical characteristic measuring system capable of estimating and calculating a visual acuity of an eye under test based on light amount intensity distribution characteristic of a target image projected on a fundus of the eye.

In the past, the present applicant has already filed a patent application for a system, which comprises a target projecting system for projecting a target image to an ocular fundus of an eye under test, and a photodetection optical system for guiding the target image to a photoelectric detector. Based on light amount intensity distribution of the target image detected by the photoelectric detector, the system calculates a simulation image on the fundus, which would be formed when the target image is projected to the fundus of the eye under test. Then, the system can identify what kind of image is formed on the fundus of the eye under test.

The system as described above provides an effect such that it is possible to calculate and identify in what condition various types of target images are projected to the fundus of the eye under test without actually projecting the various types of target images.

However, in the above system already in application, an image itself obtained by simulation can be observed, while, with respect to the visual acuity value, a visual acuity value of the eye under test must be estimated by the tester himself based on the result of observation. In this respect, there has been problem that it is difficult to find accurate visual acuity value.

SUMMARY OF THE INVENTION

To solve the above problems of the conventional type eye's optical characteristic measuring system used in the past, it is an object of the present invention to provide a system, by which it is possible to obtain an accurate visual acuity value objectively from measurement data without asking the result of the observation to a person under test.

To attain the above object, the eye's optical characteristic measuring system according to the present invention comprises a target projecting system for projecting a target image to an ocular fundus of an eye under test, a photodetection optical system for guiding the target image to a photoelectric detector, a simulation image calculating unit for calculating images of the target image to be formed when a plurality of target images of different sizes are independently projected to the fundus of the eye under test based on light amount intensity distribution of the target image detected at the photoelectric detector, and a visual acuity calculating unit having a predetermined threshold value and used for detecting light amount distribution characteristics from each of the light amount intensity distribution in a predetermined longitudinal direction of a plurality of target images calculated at the simulation image calculating unit and for calculating a visual acuity value of a person under test from an intersection of the light amount distribution characteristics and the threshold value. Also, the present invention provides the eye's optical characteristic measuring system as described above, wherein the light amount distribution characteristics are a contrast value—visual acuity curve calculated based on the maximal value and the minimal value of the light amount intensity distribution. Further, the present invention provides the eye's optical characteristic measuring system as described above, wherein the threshold value is a modulation threshold. Also, the present invention provides the eye's optical characteristic measuring system as described above, wherein a plurality of modulation threshold are prepared to correspond to different age groups respectively, and a modulation threshold corresponding to each person under test is used.

DETAILED DESCRIPTION OF THE PREFERRED EMBODIMENT

Figure 1:
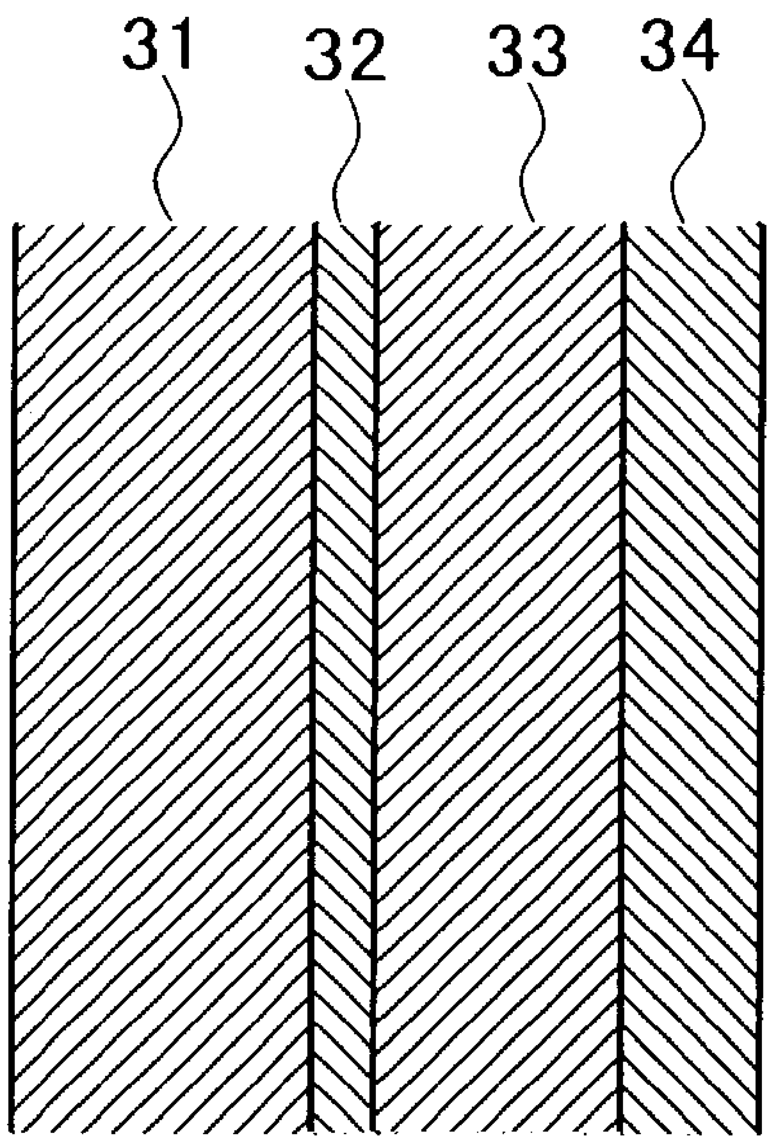
FIG. 1 is a schematical drawing of an ocular fundus of a human eye.

Description will be given below on an embodiment of the present invention referring to the drawings.

First, brief description will be given on tissues of an ocular fundus of a human eye.

FIG. 1 is a schematical drawing of tissues of an ocular fundus of a human eye. Reference numeral 31 denotes a visual cell layer, 32 is a retinal pigment epithelial layer, 33 is a choroidal membrane, and 34 is a sclera.

The visual cell layer 31 is an aggregation of fibrous visual cells aligned perpendicularly to the retinal pigment epithelial layer 32. A light beam passing through the visual cell layer 31 (visual cell) is reflected with mirror reflection by the retinal pigment epithelial layer 32. On the other hand, a part of the light beam passes through the retinal pigment epithelial layer 32 and is reflected with scattering reflection by the choroidal membrane 33 and the sclera 34 positioned behind. However, the light reflected with scattering reflection exerts almost no influence on an image to be observed and recognized by a person.

It is demonstrated in the experiment that, when the light beam entering the visual cell layer 31 passes through the visual cell, the light beam passes through it by repeating the reflection almost similar to total reflection in the visual cell.

Figure 2:
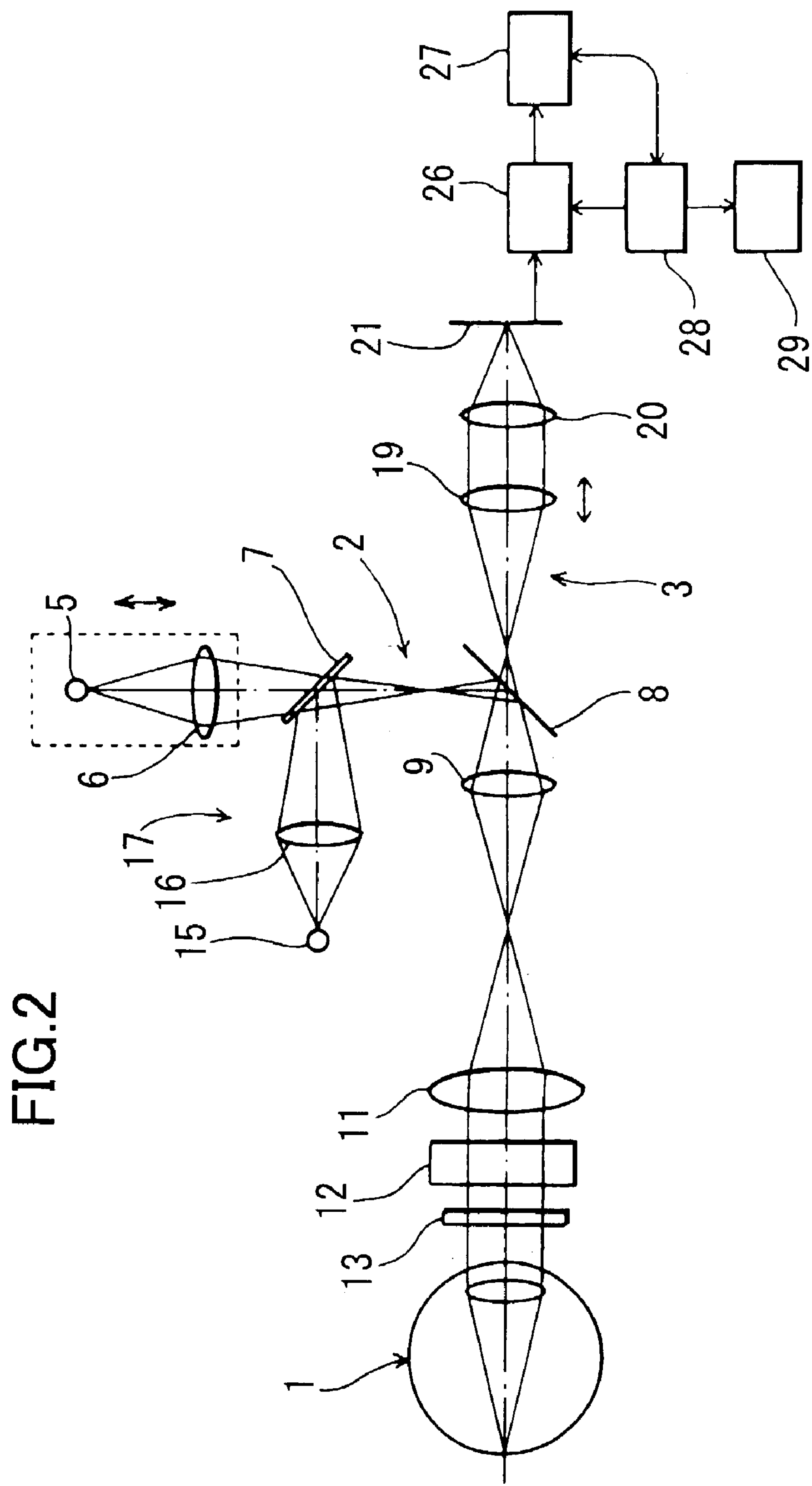
FIG. 2 is a basic block diagram of an eye's optical characteristic measuring system according to an embodiment of the present invention.

FIG. 2 shows a basic block diagram of an eye's optical characteristic measuring system according to an embodiment of the present invention.

In this figure, reference numeral 1 is an eye under test, 2 is a target projecting optical system for projecting a target image, and 3 is a photodetection optical system for receiving the light beam reflected from the eye under test.

The projecting optical system 2 comprises a light source 5, a projection lens 6 for converging a projected light beam emitted from the light source 5, a half-mirror 7 arranged on an optical axis of the projection lens 6, a polarization beam splitter 8 for directing the projected light beam passing through the half-mirror 7, for reflecting and projecting a linear polarization component (P linearly polarized light) in a first direction of polarization toward the eye 1 under test and for allowing S linearly polarized light having a direction of polarization deviated by 90° from P linearly polarized light to pass, a relay lens 9 arranged on a projection optical axis of the polarization beam splitter 8 closer to the polarization beam splitter 8 side, an objective lens 11, a correction optical system 12 arranged between the objective lens 11 and the eye 1 under test and comprising a spherical lens, and a ¼ wave plate 13. Further, a gaze target system 17 is arranged to face to the half-mirror 7 and comprises a gaze target 15 and a condenser lens 16. The light source 5 and the gaze target 15 are placed at positions conjugate to the ocular fundus of the eye 1 under test. As to be described later, the light source 5 and the gaze target 15 form an image on the ocular fundus. The light source 5 is integrated with the projection lens 6, and these can be moved in a direction of the optical axis in linkage with a focusing lens 19 (to be described later).

The photodetection optical system 3 shares the following components with the projecting optical system 2: the polarization beam splitter 8, the relay lens 9 arranged on the projection optical axis of the polarization beam splitter 8, the objective lens 11, the correction optical system 12, and the ¼ wave plate 13.

On an optical axis of the reflected light passing through the polarization beam splitter 8, there are provided the focusing lens 19 movable along the reflection light optical axis and an image forming lens 20. The image forming lens 20 focus the reflection light beam on a photoelectric detector 21, which is arranged at a position conjugate to the ocular fundus of the eye 1 under test.

A photodetection signal from the photoelectric detector 21 is stored in a storage unit 27 via a signal processing unit 26. In the storage unit 27, Landolt rings for visual acuity test, which are different, for example, in sizes, are stored as a plurality of image data. The writing of data from the signal processing unit 26 to the storage unit 27 is controlled by a control unit 28. The control unit 28 comprises a simulation image calculating unit and a visual acuity calculating unit. Based on the data stored in the storage unit 27, an estimated visual acuity value is calculated by a predetermined calculating procedure, and the result of calculation is displayed on a display unit 29.

Now, description will be given on operation of the optical system.

The focusing lens 19 is positioned at a reference position, and a person with the eye 1 under test is instructed to gaze at the gaze target 15. In this case, the correction optical system 12 is set to a correction amount 0.

With the eye 1 under test gazing at the gaze target 15, a projecting light beam is projected to the ocular fundus of the eye 1 under test by the projecting optical system 2, and an image of a point light source is formed on the ocular fundus of the eye 1 under test. Visual light is used for the gaze target 15, and infrared light is used for the projected light beam.

The projected light beam (infrared light) from the light source 5 passes through the projection lens 6 and the half-mirror 7 and reaches the polarization beam splitter 8. At the polarization beam splitter 8, a P linearly polarized light component is reflected. This passes through the relay lens 9, and is projected to the ocular fundus of the eye 1 under test by the objective lens 11 and the correction optical system 12 via the ¼ wave plate 13, and a first target image is formed on the ocular fundus.

When the P linearly polarized light passes through the ¼ wave plate 13, it is turned to a right circularly polarized light. The projected light beam is totally reflected by the ocular fundus of the eye 1, and the totally reflected light beam is turned to a left circularly polarized light when it is reflected by the ocular fundus. Further, when the totally reflected light beam passes through the ¼ wave plate 13, it is turned to an S linearly polarized light, which has a direction of polarization deviated by 90° from a direction of polarization of the P linearly polarized light.

The S linearly polarized light is guided to the polarization beam splitter 8 via the correction optical system 12, the objective lens 11 and the relay lens 9. The polarization beam splitter 8 reflects the P linearly polarized light and allows the S linearly polarized light to pass. Thus, the totally reflected light beam passes through the polarization beam splitter 8 and forms an image as a second target image on the photoelectric detector 21 by the focusing lens 19 and the image forming lens 20.

Incidentally, the projected light beam projected to the ocular fundus of the eye 1 under test is not totally reflected by a surface of the fundus with mirror reflection. A part of the light beam enters into a superficial layer through the surface of the fundus and is reflected with scattering reflection, i.e. the so-called bleeding reflection occurs. When the light beam reflected with scattering reflection is received by the photoelectric detector 21 at the same time as the light beam reflected with mirror reflection, it is turned to noise in light amount intensity distribution of the second target image, and the eye's optical characteristic of the optical system of the eye cannot be accurately measured.

The condition of polarization of the light beam reflected with scattering reflection is in random status. For this reason, when the light beam passes through the ¼ wave plate 13 and is turned to a linearly polarized light, the component matching with the S linearly polarized light is restricted to a limited part. The components other than the components matching with the S linearly polarized light in the light beam reflected by scattering light are reflected by the polarization beam splitter 8. Therefore, the ratio of A to B is negligibly low, where A is the S linearly polarized light component of the light beam reflected with scattering reflection and B is the S linearly polarized light component reflected with mirror reflection at the ocular fundus of the eye 1 under test.

Accordingly, the light received by the photoelectric detector 21 is the reflected light beam with mirror reflection, which substantially removes the reflected light component with scattering reflection. By adding the ¼ wave plate 13 as a component element of the projecting optical system 2 and the photodetection optical system 3, eye's optical characteristic of the optical system of the eye can be accurately measured. The control unit 28 calculates the light amount intensity distribution characteristic, and an optical transmission function of the optical system of the eye based on a photodetection signal from the photoelectric detector 21 and also on the data stored in the storage unit 27. Further, the estimated visual acuity value of the eye 1 under test is calculated according to the optical transmission function.

Figure 3A:
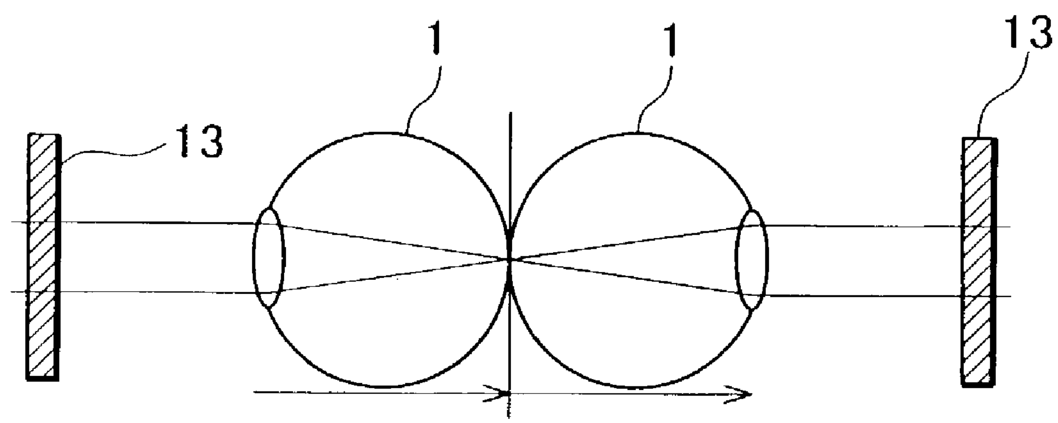
FIG. 3(A) and FIG. 3(B) each represents a drawing to show a condition of reflection at an ocular fundus of an eye under test in the eye's optical characteristic measuring system.
Figure 3B:
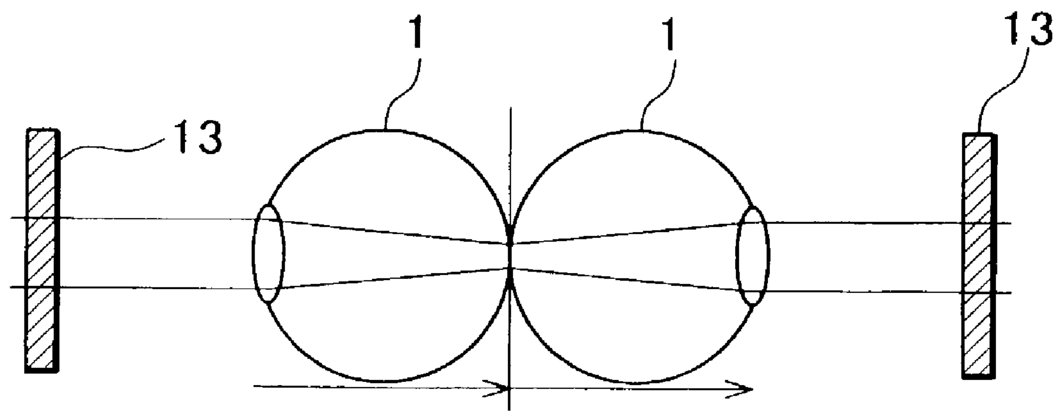

The optical characteristic of the ocular fundus can be measured by the following procedure:

FIG. 3(A) shows a condition when the light beam is focused on the ocular fundus, and FIG. 3(B) shows a condition when the light beam is not focused on the ocular fundus. Because of the influence of the detailed structure of the ocular fundus as described above, the following relationship exists under both conditions:

$$P(x,y) \supset R(x,y) \supset R(x,y) \supset P(x,y) = I(x,y) \qquad (1)$$

where P (x,y) denotes amplitude transmittance of the eye's optical system of the eye 1 under test, R (x,y) is amplitude transmittance of the visual cells including reflection characteristics at the retinal pigment epithelial layer 32, and I (x,y) is 2-demensional light amount intensity distribution to be measured on a 2-dimensional detector calculated from the photodetection signal from the 2-dimensional detector (photoelectric detector 21).

The mark ⊃ indicates convolution integration.

Next, both sides of the equation (1) are processed by Fourier transform.

Here, if it is assumed that p (u,v) is an optical transmission function of the optical system of the eye, r (u,v) is an optical transmission function of the visual cell, and i (u,v) is a 2-dimensional optical transmission function on the 2-dimensional detector, the following relationship exists:

$$FT[P(x,y)]=p(u,v)$$

$$FT[R(x,y)]=r(u,v)$$

$$FT[I(x,y)]=i(u,v)$$

By Fourier transform of the equation (1):

$$p(u,v)\times\{r(u,v)\}^2\times p(u,v)=i(u,v) \quad (2)$$

Therefore, the following equation is approximately established:

$$[p(u,v)r(u,v)]^2=i(u,v) \quad (3)$$

Then, $$p(u,v)r(u,v)=\sqrt{[i(u,v)]} \quad (4)$$

Because:

$$|FT[I(x,y)]|=i(u,v) \quad (5),$$

the 2-dimensional light amount intensity distribution I (x,y) on the 2-dimensional detector to be measured is processed by Fourier transform. The i (u,v) is obtained by the equation (5). This is substituted in the equation (4), and optical transmission function p (u,v) r (u,v) of the optical system of the eye and the visual cell are calculated.

Next, the p (u,v) r (u,v) thus calculated is processed by inverse Fourier transform, and amplitude transmittance P $(x,y)\cdot\dot{\underset{\cdot}{X}}\cdot$R (x,y) of the optical system of the eye and the visual cell is calculated.

$$IFT[p(u,v)r(u,v)]=P(x,y)\cdot\dot{\underset{\cdot}{X}}\cdot R(x,y) \quad (6)$$

By performing convolution integration on the amplitude transmittance P $(x,y)\cdot\dot{\underset{\cdot}{X}}\cdot$R (x,y) of the optical system of the eye and the visual cell thus calculated and a light amount intensity distribution function O (x,y) of a desired target for visual acuity test, a simulation image S (x,y) of an image projected on the ocular fundus of the eye under test can be calculated by the following equation:

$$S(x,y)=P(x,y)\cdot\dot{\underset{\cdot}{X}}\cdot R(x,y)\cdot\dot{\underset{\cdot}{X}}\cdot O(x,y) \quad (7)$$

Figure 4:
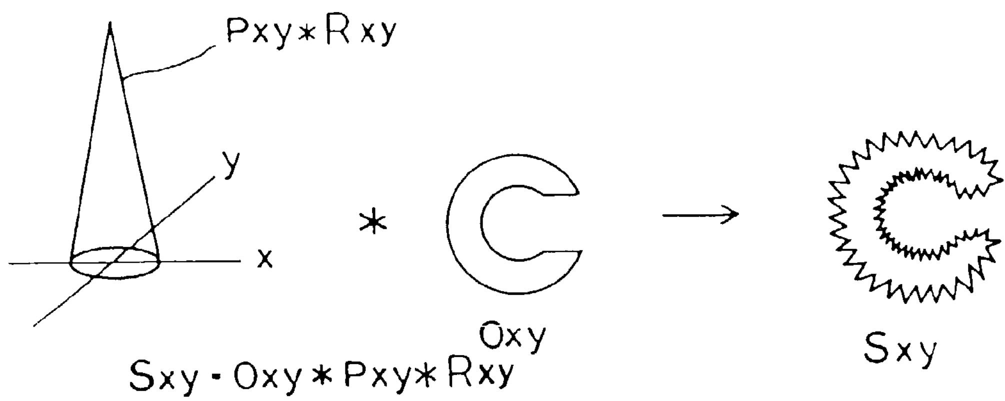
FIG. 4 is a drawing to explain a target for visual acuity test and a calculated simulation image.

FIG. 4 shows a simulation image S (x,y) of an image obtained by convolution integration of the amplitude transmittance P $(x,y)\cdot\dot{\underset{\cdot}{X}}\cdot$R (x,y) and the light amount intensity distribution function O (x,y). In the figure, the simulation image S (x,y) has notched edge, and this indicates that the image is blurred. In FIG. 4, an example of Landolt ring target is shown as the target for visual acuity test. Additionally, if a light amount intensity distribution function for various types of targets for visual acuity test such as characters, figure, etc. is selected, the simulation images S (x,y) of various types of targets can be calculated and displayed as necessary.

Figure 5:
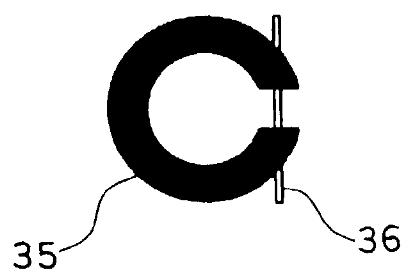
FIG. 5 is a drawing to explain a Landolt ring target and a target gap direction.
Figure 6:
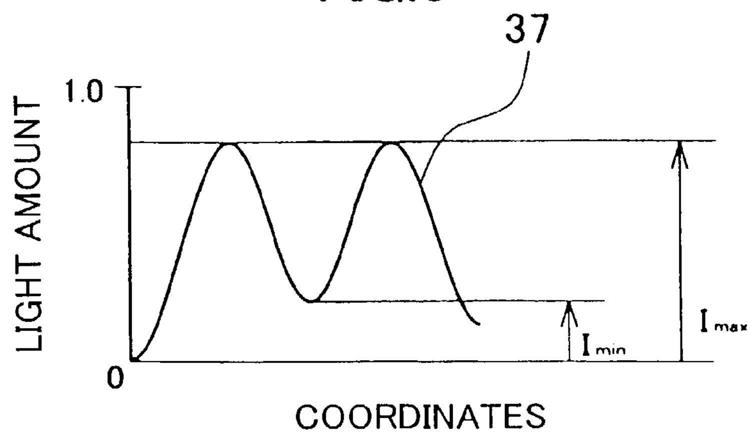
FIG. 6 is a diagram showing a profile of light amount intensity distribution in the target gap direction.

An image 35 obtained by calculation is given in FIG. 5, for instance. A profile 37 of light amount change in a direction (target gap direction 36) crossing a gap (lacked portion of Landolt ring) of the image 35 is calculated. FIG.

6 is a diagram showing the calculated profile 37 in graph. The profile 37 is calculated respectively on each target for visual acuity test corresponding to each visual acuity value. Further, based on the profile 37, a contrast value is calculated at the control unit 28.

The contrast value is obtained from the following equation (8) where Imax is the maximal value of the profile 37, and Imin is the minimal value.

$$\begin{aligned}\text{Contrast value (\%)} &= (I\max - I\min)\times 100/(I\max + I\min) \quad (8)\\ &= (1 - I\min/I\max)\times 100/(1 + I\min/I\max)\end{aligned}$$

As it is apparent from the diagram, two values for Imax are obtained. Either one of the two Imax values may be used or an average value may be used.

Figure 7A:
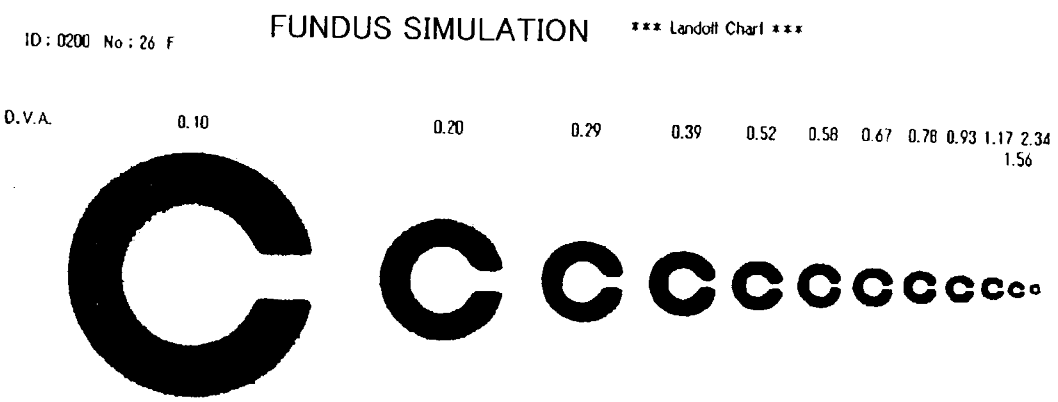
FIG. 7 shows examples of display when the simulation image, the profile and a contrast value—visual acuity curve are displayed on the same screen.
Figure 7B:
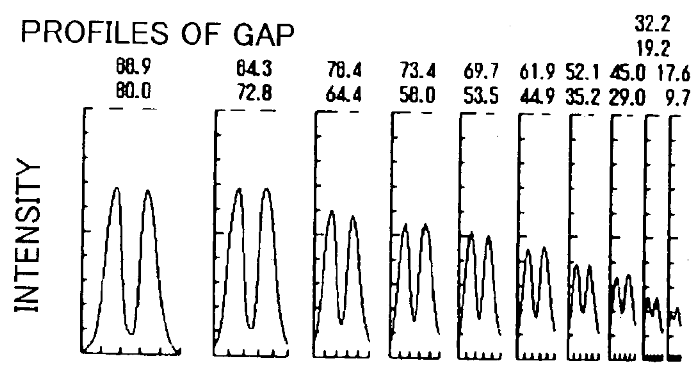
Figure 7C:
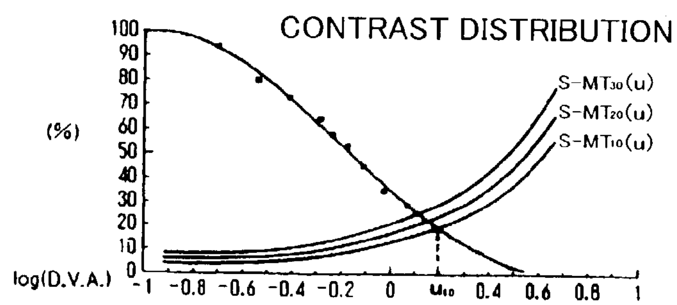

The calculated simulation images, the profiles 37, etc. are shown in comparison as given in FIG. 7.

In FIG. 7, an image Ixy of simulation image of a target for visual acuity test corresponding to each decimal visual acuity value (D.V.A.) is shown in the Column A. Profiles 37 for the lacked portion of the image Ixy corresponding to each decimal visual acuity value (D.V.A.) are shown in the Column B. A contrast value—visual acuity curve (to be described later) is shown in the Column C. In the figure, the images Ixy in the Column A have the contour gradually blurred as the visual acuity value is increased although it is not clearly indicated in the figure.

As shown in FIG. 7, the images Ixy of simulation images for the targets in visual acuity test corresponding to each decimal visual acuity value (D.V.A.) (see the Column A in FIG. 7) and the profiles 37 of the images Ixy corresponding to each decimal visual acuity value (D.V.A.) (see the Column B in FIG. 7) are obtained. Further, the maximal value and the minimal value of the profiles 37 are obtained. Based on the maximal value and the minimal value, a contrast value of each of the visual acuity values is calculated from the above equation (8). Further, by interpolating the result of calculation using a regression curve (e.g. a cubic polynomial), a contrast value of visual acuity value other than the target for visual acuity test used for simulation can be estimated. In FIG. 7, if the original target image for visual acuity test as stored in the storage unit 27 is displayed in alignment with the image Ixy, the image can be compared with each other, and visual effect can be further increased.

As described above, a curve is obtained, which is interpolated by calculation at the control unit 28. The contrast value—visual acuity curve as obtained by interpolation is shown in the Column C of FIG. 7.

In the diagram shown in the Column C of FIG. 7, contrast value is represented on the axis of ordinate, and logarithm of visual acuity value is shown on the axis of abscissa. Experimentally, it is demonstrated that the target for visual acuity test can be identified when the contrast value is approximately 15% or more.

As described above, by the contrast value—visual acuity curve thus obtained, the visual acuity value of the eye under test can be quantitatively and objectively determined. Further, a possible visual acuity value under corrected condition can be estimated. The tester can more clearly identify the optical characteristics of the eye under test from the form and features of the contrast value—visual acuity curve.

A Landolt ring is used as the target for visual acuity test in the above, while various types of targets for visual acuity test such as character chart can be used additionally. Also, the contrast value is not limited to two values of black and white. By using a gray chart, the visual value can be estimated more accurately.

In the embodiment as given above, a Landolt ring for visual acuity test having a gap is used as the gaze target 15, while a target having a plurality of gaps may be used to have higher measurement accuracy.

Next, description will be given below on a calculation procedure to estimate the visual acuity value of the eye under test based on the contrast value—visual acuity curve.

As described above, it is reported that the target for visual acuity test can be identified when the contrast value (threshold value) is approximately 15% or more, while there are differences due to personal difference or to the age of the person under test. Therefore, error may be increased if the threshold is set to a constant value for all persons under test. In the present invention, a constant threshold value is not used as a threshold value. As a threshold value of nervous system in the visual system, the so-called modulation-threshold (hereinafter referred as "MT(u)") is used as the threshold value to have higher measurement accuracy.

The MT (u) can be experimentally obtained by entering two light beams to the eye to directly form interference fringes on the retina of the fundus and by instructing a person to observe the condition of the interference fringes. The MT (u) thus obtained is sinusoidal wave MT (u). The value used as the threshold value for estimating visual aquity is square-MT to square wave (hereinafter referred as "S-MT"), and this is converted from the sinusoidal wave MT (u).

The conversion can be made by the following equation:

$$S\text{-}MT(u)=4/\pi\{MT(u)-(MT(3u))/3+(MT(5u))/5-(MT(7u))/7+\ldots\} \quad (9)$$

The S-MT (u) obtained here indicates a boundary value, which can be identified by the eye under test. If the value is higher than S-MT (u), it can be identified by the eye under test. If the value is lower than S-MT (u), it cannot be identified by the eye under test.

The S-MT (u) as described above generally varies according to age of the person under test. There are prepared S-MT10 (u) defined for teen-agers, S-MT20 (u) defined for those in the twenties, and S-MT30 (u) defined for those in the thirties . . . . Using the modulation-threshold corresponding to the age of the person under test, the visual acuity corresponding to an intersection of S-MT (u) and the contrast value—visual acuity curve of the person under test is calculated. For instance, in case the person under test is a teen-ager, a visual acuity value log (D.V.A.) corresponding to an intersection of S-MT10 and the contrast value—visual acuity curve is obtained in FIG. 7(C). The relation between the decimal visual acuity value (D.V.A.) and u is given by: D.V.A.=u/100.

Thus, the visual acuity value is obtained by using the threshold value corresponding to MT (u) of the age of the person under test, and error in the estimated value can be reduced. Also, the visual acuity value of the eye under test can be determined without relying on the answer from the person under test. Further, a simulation image corresponding to an image perceived by the person under test can be obtained at real time.

In the present embodiment, description is given on such case that the position of the focusing lens 19 is regarded as the reference position, and the correction optical system 12 is set to correction amount 0, and the measurement is performed. Based on the result of the measurement, the visual acuity value of the naked eye of the person under test is estimated. The present invention is not limited to this case, and a visual acuity value after correcting the refraction of a certain amount can be also estimated if the correction optical system is adjusted or the focusing lens is moved, and measurement is made after correction of refraction of a certain amount and by performing similar calculation.

The eye's optical characteristic measuring system according to the present invention comprises a target projecting system for projecting a target image to an ocular fundus of an eye under test, a photodetection optical system for guiding the target image to a photoelectric detector, a simulation image calculating unit for calculating images of the target image to be formed when a plurality of target images of different sizes are independently projected to the fundus of the eye under test based on light amount intensity distribution of the target image detected at the photoelectric detector, and a visual acuity calculating unit having a predetermined threshold value and used for detecting light amount distribution characteristics from each of the light amount intensity distribution in a predetermined longitudinal direction of a plurality of target images calculated at the simulation image calculating unit and for calculating a visual acuity value of a person under test from an intersection of the light amount distribution characteristics and the threshold value. As a result, the visual acuity value of the eye under test can be accurately estimated by calculating procedure by projecting a predetermined target image to the ocular fundus of the eye and by simply measuring the light amount intensity distribution of the target image without using the so-called subjective visual acuity test in the procedure to measure visual acuity value based on an answer of a person under test after showing a target for visual acuity test of various sizes to the person under test.

What is claimed is:

1. An eye's optical characteristic measuring system, comprising a target projecting system for projecting a target image on an ocular fundus of an eye under test, a photodetection optical system for guiding the target image to a photoelectric detector after said target image impinges on the ocular fundus, a simulation image calculating unit for calculating images that are modified versions of the original target image based on the convolution of an actual intensity distribution function, and a visual acuity calculating unit having a predetermined threshold value and used for detecting light amount distribution characteristics from the light amount intensity distribution in a predetermined longitudinal direction of each of the modified versions calculated at said simulation image calculating unit and for calculating a visual acuity value of a person under test from an intersection of the light amount distribution characteristics and said threshold value.

2. An eye's optical characteristic measuring system according to claim 1, wherein said light amount distribution characteristics are a contrast value—visual acuity curve calculated based on the maximal value and the minimal value of the light amount intensity distribution.

3. An eye's optical characteristic measuring system according to claim 1, wherein said threshold value is a modulation threshold.

4. An eye's optical characteristic measuring system according to claim 3, wherein a plurality of modulation threshold are prepared to correspond to different age groups respectively, and a modulation threshold corresponding to each person under test is used.

* * * * *